(12) United States Patent
Phillips, Jr. et al.

(10) Patent No.: US 10,174,933 B2
(45) Date of Patent: Jan. 8, 2019

(54) POSITIONABLE TOOL LIGHT

(71) Applicant: Green Lite Innovations, LLC, Cottonwood Heights, UT (US)

(72) Inventors: Gregory Douglas Phillips, Jr., Steilacoom, WA (US); Matthew Neil Lamont, Highland, UT (US); Banjamin Harris Timmins, Salt Lake City, UT (US); Quinn Tate, Salt Lake City, UT (US); Jonathan LeGrand Curtis, Cottonwood Heights, UT (US); Theodore Espiritu, Salt Lake City, UT (US)

(*) Notice: Subject to any disclaimer, the term of this patent is extended or adjusted under 35 U.S.C. 154(b) by 0 days.

(21) Appl. No.: 15/799,860

(22) Filed: Oct. 31, 2017

(65) Prior Publication Data
US 2018/0156448 A1 Jun. 7, 2018

Related U.S. Application Data

(60) Provisional application No. 62/415,382, filed on Oct. 31, 2016.

(51) Int. Cl.
| F21L 4/02 | (2006.01) |
| F21V 33/00 | (2006.01) |
| A61B 1/06 | (2006.01) |
| A61B 90/30 | (2016.01) |
| A61B 1/32 | (2006.01) |
| A61B 1/303 | (2006.01) |
| F21L 4/00 | (2006.01) |
| F21V 21/08 | (2006.01) |
| A61B 1/24 | (2006.01) |

(Continued)

(52) U.S. Cl.
CPC .......... *F21V 33/0068* (2013.01); *A61B 1/06* (2013.01); *A61B 1/0684* (2013.01); *A61B 1/303* (2013.01); *A61B 1/32* (2013.01); *A61B 90/30* (2016.02); *F21L 4/00* (2013.01); *F21L 4/025* (2013.01); *F21V 21/0808* (2013.01); *A61B 1/24* (2013.01); *A61B 1/267* (2013.01); *A61B 13/00* (2013.01); *F21V 33/0084* (2013.01); *F21Y 2115/10* (2016.08)

(58) Field of Classification Search
CPC ... F21V 33/0068; F21V 21/0808; A61B 1/06; A61B 1/24; A61B 1/32; A61B 1/303; A61B 90/30; F21L 4/025; F21L 4/00
See application file for complete search history.

(56) References Cited

U.S. PATENT DOCUMENTS

| 8,727,919 B1 * | 5/2014 | Gentile | A63B 43/06 473/570 |
| 2001/0049311 A1 * | 12/2001 | Lewis | A63B 43/06 473/570 |

* cited by examiner

Primary Examiner — Thomas M Sember
(74) Attorney, Agent, or Firm — Dobbin IP Law P.C.; Geoffrey E. Dobbin

(57) ABSTRACT

A positionable lighting unit for tools may have an LED light source powered by a battery with a control switch, all mounted upon a circuit board encased within a translucent and flexible casing. The control switch may then be activated though the casing without breaching the same so that a more sterile unit may be presented in those situations requiring sterility. The tool light also may have an adhesive, so it may be temporarily positioned according to a user's liking on a given tool. Emphasis is given to medical devices where a small field of vision and little room for movement may be prohibitive of desired lighting placement, but the light may be used on any suitable tool in any suitable medical or non-medical situation.

8 Claims, 5 Drawing Sheets

(51) Int. Cl.
*F21Y 115/10* (2016.01)
*A61B 1/267* (2006.01)
*A61B 13/00* (2006.01)

14

16  18  22

POSITIONABLE TOOL LIGHT

CROSS-REFERENCES TO RELATED APPLICATIONS

This Application claims priority as a non-provisional perfection of prior filed U.S. application No. 62/415,382, filed Oct. 31, 2016, and incorporates the same by reference herein in its entirety.

FIELD OF THE INVENTION

The present invention relates to the field of lighting and more particularly relates to a small, attachable light for use with hand tools, but with particular use in the medical field.

BACKGROUND OF THE INVENTION

It is a well-known fact that not being able to see makes evaluation of a subject and subsequent action difficult. We use our eyes to evaluate a situation or an object, orient our actions, and guide the same. Therefore, darkness can be a great inhibition to efficient action. Often it is necessary to evaluate or move in a small and dark area. To counter this possibility, lights have been made to fit within cramped spaces, usually placed on tools used in whatever operation the user desired to perform. Small lighting tools may then be positioned in an area efficiently to illuminate what was once obscured. However, there is a trade-off. When placing a light in an enclosed volume, there is a risk of continued obscurement as the light itself will physically block a portion of the field of view. There is also the risk that the light structure will be in the way of any action required to be taken. Therefore, it is advantageous to not only have a light which presents a small view profile, but also presents little physical impediment to movement in the area. A light that is positionable by the user, therefore, presents an advantage over lights which are statically relocated. Activation of the lights may also prove problematic, especially in medical contexts. A switch, which is by its nature usually a moving part, usually has some small orifice, either where one piece of the switch was, or to where it is moving, where microbes may inhabit and grow.

The present invention is a small light source attachable to a tool for illuminating a small volume into which the tool is positioned. The light source presents a very narrow width, and thus presents a narrow sight profile. It also is very little height to not inhibit movement within a volume. Among these features, the light source has an adhesive backing, so it may be temporarily positioned anywhere convenient on the tool, as determined by the user. The light source is also encased in a soft shell so that it may be used in medical procedures when the shell is of suitable material and a small internal switch is provided so that the shell need not be opened or broken to activate the light.

The present invention represents a departure from the prior art in that the positionable light of the present invention allows for convenient positioning of the light source on the tool being used in a procedure so that it presents a limited impediment to sight and action.

SUMMARY OF THE INVENTION

In view of the foregoing disadvantages inherent in the known types of tool lights, this invention provides a low-profile light source for use on a tool. As such, the present invention's general purpose is to provide a new and improved light source that is small and unobtrusive while easy to install and operate.

To accomplish these objectives, the preferred embodiment of the lighting unit comprises a circuit board with a power source, LED, operable circuitry and a push switch all encased in a sealed medical grade, flexible cover. The cover also features an adhesive, protected by a liner until desired use. In use, the operator will remove the release liner and position the lighting unit on a tool in a manner of the operator's discretion. In so doing, the low profile of the lighting unit will then be utilized to the operator's liking, balancing desired view and movement with illumination.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for general description only and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

Figure 1:
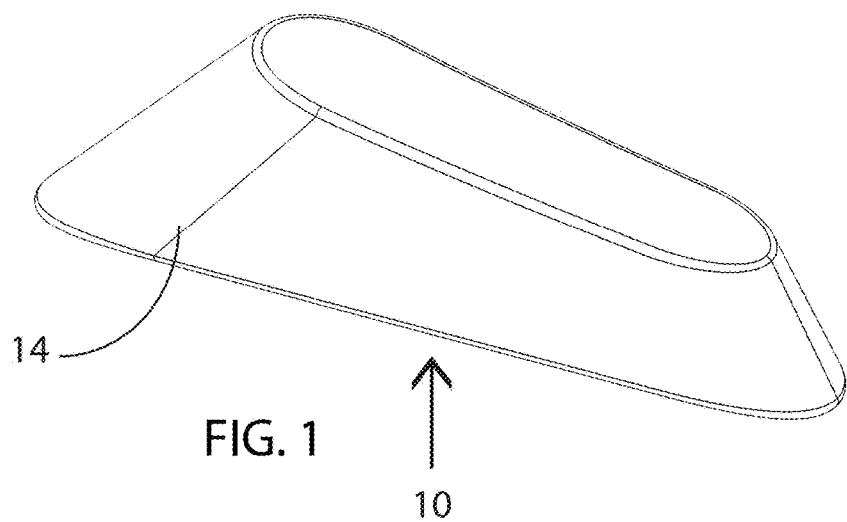
FIG. 1 is a perspective view of one embodiment of the positionable tool light.
Figure 2:
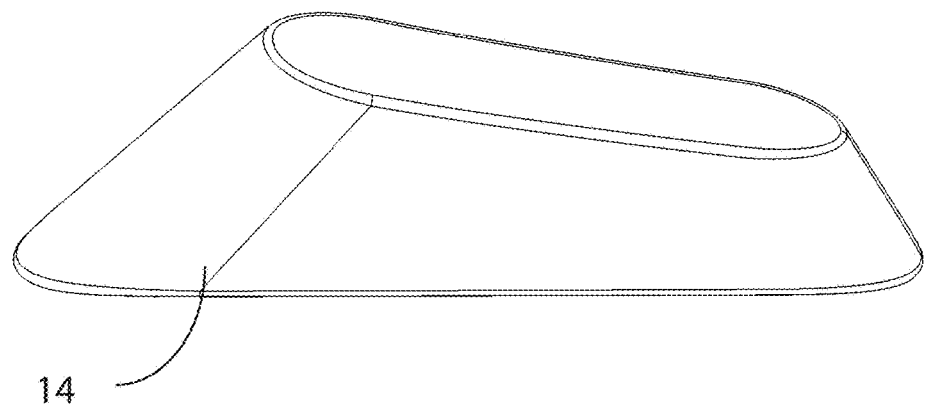
FIG. 2 is a side perspective view of the positionable tool light of FIG. 1.
Figure 3:
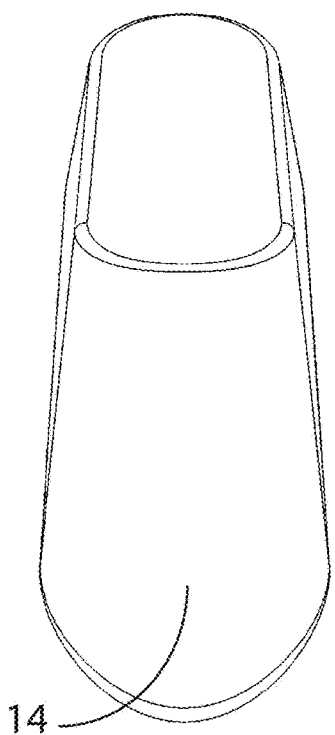
FIG. 3 is a front perspective view of the positionable tool light of FIG. 1.
Figure 4:
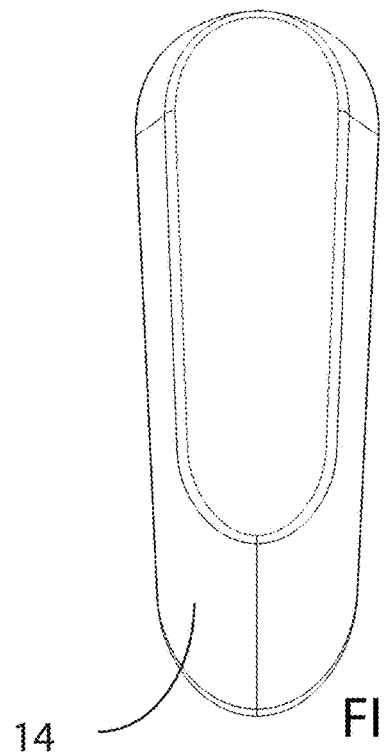
FIG. 4 is a rear perspective view of the positionable tool light of FIG. 1.
Figure 5:
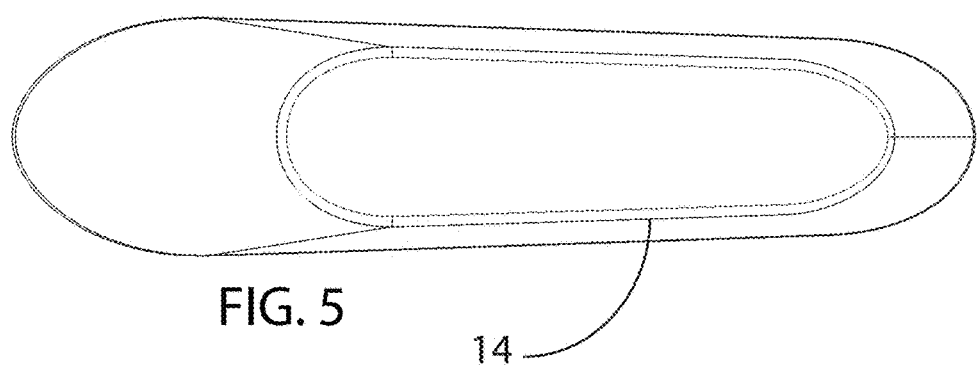
FIG. 5 is a top plan view of the positionable tool light of FIG. 1.
Figure 6:
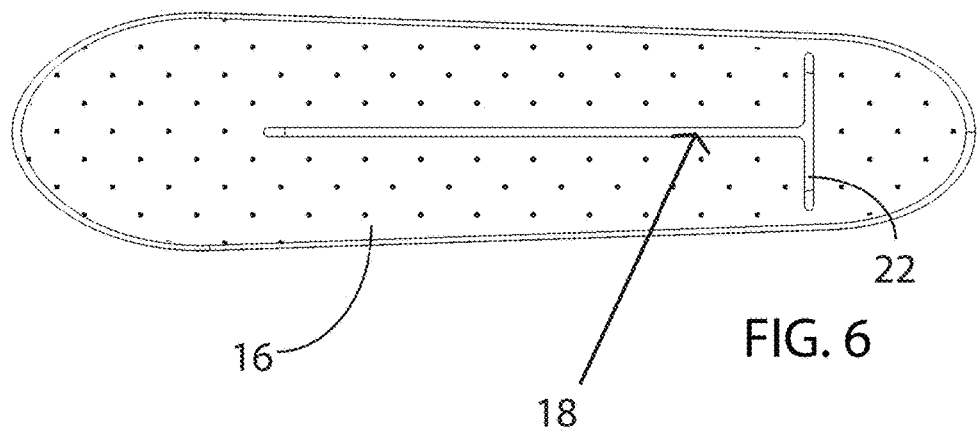
FIG. 6 is a bottom plan view of the positionable tool light of FIG. 1.

With reference now to the drawings, the preferred embodiment of the positionable lighting unit is herein described. It should be noted that the articles "a", "an", and "the", as used in this specification, include plural referents unless the content clearly dictates otherwise.

With reference to FIGS. 1-6, and 9 the positionable tool light 10 is encased in a protective cover 14. The cover 14 contains a light unit 20 and protects the same from the external environment. As such, the cover 14 should be a total, flexible encasement, with no openings. Though an opening 18 (FIG. 6) may be initially provided to insert light unit 20 inside the cover 14, it should be immediately sealed to lessen contamination risk and to secure the light unit 20 inside the cover 14. Ideally, an adhesive 16 (dotted surface, FIG. 6) is applied to a surface of the cover 14 and covered by a release liner (not shown) until the tool light 10 is ready for use. However, other means of mounting the tool light 10 are possible, especially if not used in the medical field. As a switch 24 is included on the light unit 20, the flexibility of the cover 14 allows for the activation of the light unit 20 without breaching the cover 14. This has importance when using the tool light 10 in a medical context—sterility of the unit is preserved by preventing any microbial infestation of the internal light unit 20, including the switch 24, or of a passage through the cover 14 are eliminated.

Figure 7:
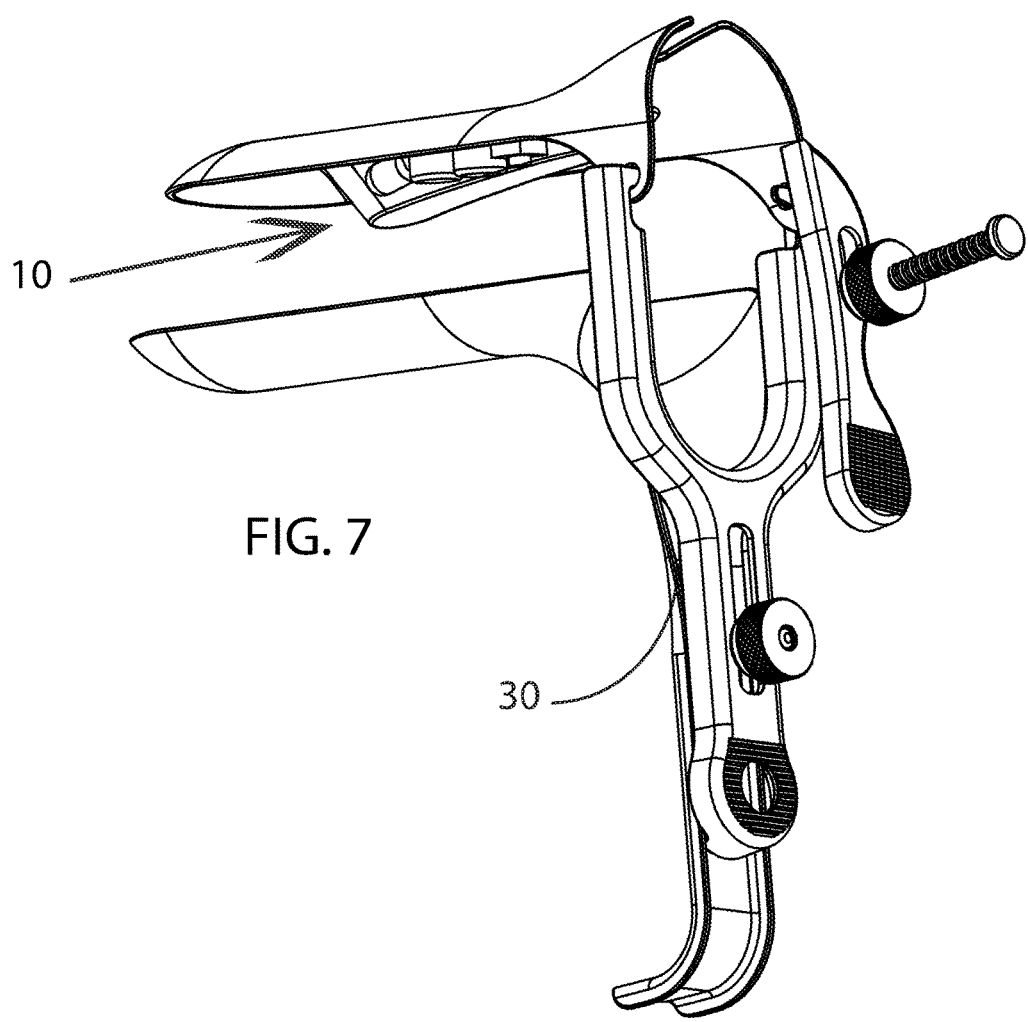
FIG. 7 is a perspective view of the positionable tool light of FIG. 1, mounted upon a vaginal speculum.
Figure 8:
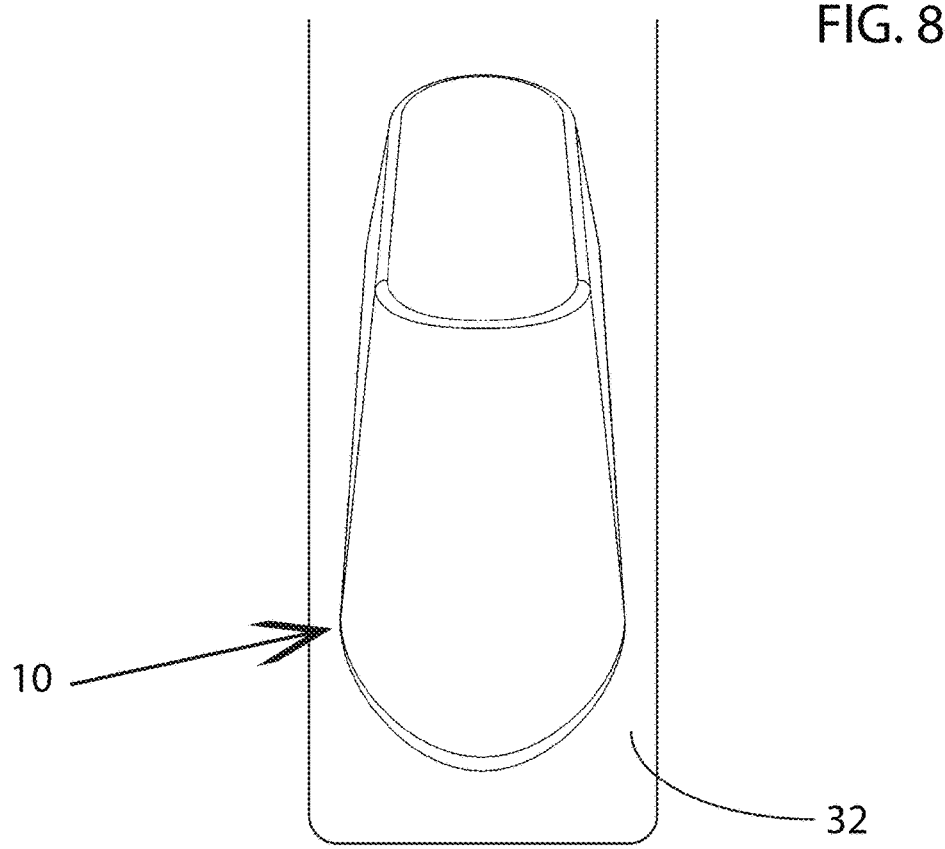
FIG. 8 is a perspective view of the positionable tool light of FIG. 1, mounted upon a tongue depressor.

The tool light 10 may be positioned on any tool. As illustrated in FIGS. 7 and 8, the tool light 10 may be positioned on an internal portion of the bills of a vaginal speculum 30. Other tools, such as a tongue depressor 32 or laryngoscope, may also benefit by the addition of the tool light 10. In either case, the low and narrow profile of the tool light 10 allows for an easier mounting on the tool and provides a greater and mostly unobstructed field of view with bright and shadow free illumination of the work area, which in the medical field would often be a small body cavity. It should be noted that while the illustrated tools are two medical devices, the tool light 10 may be positioned on any type of tool by means of the adhesive layer 16, ideally positioned upon the bottom of the lighting unit cover 14. This would include industrial tools and other medical devices—any tool used in a small and consequently dark area. Positioning the tool light 10 is also easily adaptable to the preference of the user and the environmental situation, such as, in a medical context, the variability of human anatomy and type of procedure performed. After positioning, the tool light 10 may be activated by depressing the switch 24, as the flexible cover 14 is displaceable to allow for such depression, and the tool is then used according to its purpose. In the medical context, activation of the switch 24 does not require breaking the cover 14, reducing possible contamination of the area. After use, the tool light 10 may be either removed from the tool or if the tool is itself disposable, as is frequently the case with medical devices, then the tool light 10 may be disposed with the tool.

Figure 9:
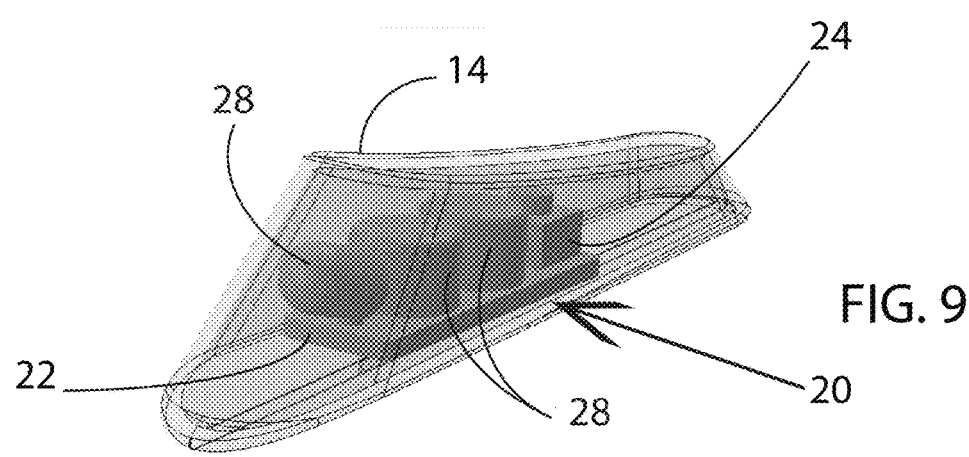
FIG. 9 is a transparent perspective view of the positionable tool light of FIG. 1.

The light unit 20 base should be a printed circuit board (PCB), shown best in FIG. 9, which is ideally long and narrow and features only necessary components. Circuitry may run along both the upper and lower side of the PCB 22 to minimize space. Switch 24 is provided to activate the light source, ideally an LED 26 as LEDs are small and produce only a small amount of heat. The LED 26 is preferred to be white in most contexts, though any other color is possible, including light wavelengths that are in some way reactive to specific tissues, materials, or dyes introduced to a body or area. The switch 24 is ideally a single button depressible switch so that it may be easily manipulated through the cover 14. A power source, such as battery 28, is also provided as is circuitry required for functionality. Currently, the ideal circuit board 22 should measure no more than 3 by 1 centimeters, but other dimensions are possible depending on intended use of the tool light 10 and the availability of later developed technologies. The adhesive 16 and cover 14 should be medical grade in those situations for medical use, but this is not required for other uses. Cover 14 should also be flexible and clear, or at the very least have a clear area towards the light source 26 to allow light transmission. The shape of the cover may be curved, to fit inside a specula bill with maximum surface contact, or flat, such as for a tongue depressor.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A tool light comprising:
    a flexible cover defining an external surface and an internal volume, the flexible cover being, at least partially, capable of light transmission therethrough; and
    a light source disposed entirely within the internal volume of the flexible cover, the light source further comprising:
        a printed circuit board,
        a power source,
        a light source, and
        a depressible switch;
    an adhesive applied to one part of the external surface of the flexible cover; and
    a tool having an external surface upon which the flexible cover is mounted by the adhesive;
    wherein the light source is totally encased in the flexible cover and isolated from an external environment and the depressible switch is activated without breaching the flexible cover.

2. The tool light of claim 1, further comprising an adhesive on at least a part of the external surface of the flexible cover.

3. The tool light of claim 2, the light source being at least one LED.

4. The tool light of claim 1, the light source being at least one LED.

5. The tool light of claim 1, the tool being selected from the set of tools consisting of a tongue depressor, laryngoscope, and a speculum.

6. The tool light of claim 5, further comprising an adhesive on at least a part of the external surface of the flexible cover.

7. The tool light of claim 6, the light source being at least one LED.

8. The tool light of claim 5, the light source being at least one LED.

* * * * *